US009475264B2

(12) United States Patent
Melander

(10) Patent No.: US 9,475,264 B2
(45) Date of Patent: Oct. 25, 2016

(54) UNDERWEAR ARTICLE COMPRISING AN ELASTIC LAMINATE

(75) Inventor: Magnus Melander, Gothenburg (SE)

(73) Assignee: SCA HYGIENE PRODUCTS AB, Göteborg (SE)

(*) Notice: Subject to any disclaimer, the term of this patent is extended or adjusted under 35 U.S.C. 154(b) by 948 days.

(21) Appl. No.: 11/845,153

(22) Filed: Aug. 27, 2007

(65) Prior Publication Data

US 2008/0000003 A1 Jan. 3, 2008

Related U.S. Application Data

(63) Continuation of application No. PCT/SE2005/000318, filed on Mar. 2, 2005.

(51) Int. Cl.
A01B 27/00 (2006.01)
B32B 27/12 (2006.01)
A61F 13/49 (2006.01)
A61F 13/496 (2006.01)
B32B 25/04 (2006.01)
A61F 13/15 (2006.01)

(52) U.S. Cl.
CPC ........... B32B 27/12 (2013.01); A61F 13/4902 (2013.01); A61F 13/496 (2013.01); B32B 25/04 (2013.01); A61F 2013/15292 (2013.01); A61F 2013/15406 (2013.01); A61F 2013/15552 (2013.01); B32B 2250/03 (2013.01); B32B 2250/40 (2013.01); B32B 2262/0253 (2013.01); B32B 2307/51 (2013.01); B32B 2307/581 (2013.01); B32B 2309/14 (2013.01); B32B 2555/02 (2013.01)

(58) Field of Classification Search
CPC . A42B 2400/52; A42B 9/001; A61F 13/496; A61F 13/565; Y10T 442/674
USPC .............. 2/109, 400–405, 67; 604/396, 365; 428/198; 442/394
See application file for complete search history.

(56) References Cited

U.S. PATENT DOCUMENTS 3,259,539 A   7/1966 Katz et al.
3,424,162 A * 1/1969 Parravicini ................... 604/396
(Continued)

FOREIGN PATENT DOCUMENTS

CO  2007-003796  1/2008
EP  0 287 388 A2  10/1988
(Continued)

OTHER PUBLICATIONS

English Translation of the Decision on Grant Patent for Invention issued in corresponding paten application No. RU 2007136282.
(Continued)

*Primary Examiner* — Richale Quinn
(74) *Attorney, Agent, or Firm* — Buchanan Ingersoll & Rooney PC

(57) ABSTRACT

A pant-type underwear article 10, having a front 12, back 14, crotch 16 and waist 18 regions, the article 10 having a longitudinal (y) and a transverse direction (x). At least part of the article 10 has an elastic laminate 20 composed of first 22 and second 24 layers of fibrous material and an elastic film layer 26 located between the first and second fibrous layers 22, 24, the elastic laminate 20 having a puncture resistance of at least 15N.

24 Claims, 5 Drawing Sheets

(56) References Cited

U.S. PATENT DOCUMENTS

| | | | |
|---|---|---|---|
| 4,119,450 A | 10/1978 | Bianco | |
| 4,663,220 A | 5/1987 | Wisneski et al. | |
| 4,698,261 A | 10/1987 | Bothe et al. | |
| 4,739,012 A * | 4/1988 | Hagman | 525/92 A |
| 4,777,080 A | 10/1988 | Harris, Jr. et al. | |
| 4,842,596 A | 6/1989 | Kielpikowski et al. | |
| 4,850,990 A | 7/1989 | Huntoon et al. | |
| 4,932,949 A | 6/1990 | Thygesen et al. | |
| 4,965,122 A | 10/1990 | Morman | |
| 5,098,419 A * | 3/1992 | Gold | 604/396 |
| 5,114,781 A | 5/1992 | Morman | |
| 5,143,679 A | 9/1992 | Weber et al. | |
| 5,156,793 A | 10/1992 | Buell et al. | |
| 5,167,897 A | 12/1992 | Weber et al. | |
| 5,261,899 A | 11/1993 | Visscher et al. | |
| 5,336,545 A | 8/1994 | Morman | |
| 5,422,172 A | 6/1995 | Wu | |
| 5,440,764 A * | 8/1995 | Matsushita | 2/401 |
| 5,462,541 A | 10/1995 | Bruemmer et al. | |
| 5,514,470 A | 5/1996 | Haffner et al. | |
| 5,592,690 A * | 1/1997 | Wu | 2/67 |
| 5,628,738 A * | 5/1997 | Suekane | 604/385.26 |
| 5,634,216 A | 6/1997 | Wu | |
| 5,635,290 A * | 6/1997 | Stopper et al. | 428/198 |
| 5,706,524 A | 1/1998 | Herrin et al. | |
| 5,733,628 A | 3/1998 | Pelkie | |
| 5,746,730 A * | 5/1998 | Suzuki et al. | 604/385.26 |
| 5,769,838 A * | 6/1998 | Buell et al. | 604/396 |
| 5,861,074 A | 1/1999 | Wu | |
| 5,921,973 A * | 7/1999 | Newkirk et al. | 604/365 |
| 6,023,789 A * | 2/2000 | Wilson et al. | 2/228 |
| 6,072,005 A | 6/2000 | Kobylivker et al. | |
| 6,106,925 A | 8/2000 | Palumbo | |
| 6,210,386 B1 | 4/2001 | Inoue | |
| 6,240,569 B1 * | 6/2001 | Van Gompel et al. | 2/400 |
| 6,476,289 B1 | 11/2002 | Buell et al. | |
| 6,540,731 B2 | 4/2003 | Magnussson et al. | |
| 6,552,245 B1 | 4/2003 | Roessler et al. | |
| 6,585,713 B1 | 7/2003 | LeMahieu et al. | |
| 6,627,564 B1 * | 9/2003 | Morman et al. | 442/327 |
| 6,848,121 B1 * | 2/2005 | Halid | 2/400 |
| 6,914,018 B1 | 7/2005 | Uitenbroek et al. | |
| 7,211,531 B2 | 5/2007 | Schneider | |
| 7,320,948 B2 | 1/2008 | Morman et al. | |
| 7,722,591 B2 * | 5/2010 | Back | 604/385.31 |
| 7,806,884 B2 * | 10/2010 | Hildeberg et al. | 604/385.27 |
| 7,824,389 B2 | 11/2010 | Veith | |
| 8,052,665 B2 | 11/2011 | Wastlund-Karlsson et al. | |
| 8,109,916 B2 | 2/2012 | Wennerback | |
| 8,298,205 B2 | 10/2012 | Norrby et al. | |
| 9,102,132 B2 | 8/2015 | Wennerback | |
| 9,271,880 B2 | 3/2016 | Karlson et al. | |
| 2002/0002021 A1 | 1/2002 | May et al. | |
| 2002/0004350 A1 | 1/2002 | Morman et al. | |
| 2002/0019187 A1 * | 2/2002 | Carroll et al. | 442/394 |
| 2002/0029026 A1 | 3/2002 | Furuya et al. | |
| 2002/0052591 A1 | 5/2002 | Zehner et al. | |
| 2003/0022582 A1 | 1/2003 | Cree et al. | |
| 2003/0078558 A1 * | 4/2003 | Karami et al. | 604/391 |
| 2003/0088230 A1 | 5/2003 | Balogh et al. | |
| 2003/0091807 A1 | 5/2003 | Desai et al. | |
| 2003/0105446 A1 | 6/2003 | Hutson et al. | |
| 2003/0124310 A1 | 7/2003 | Ellis et al. | |
| 2003/0135184 A1 | 7/2003 | Van Gompel et al. | |
| 2004/0073188 A1 | 4/2004 | Mitsui et al. | |
| 2004/0078018 A1 * | 4/2004 | Gompel et al. | 604/385.16 |
| 2004/0087235 A1 | 5/2004 | Morman et al. | |
| 2004/0102746 A1 | 5/2004 | Mortell et al. | |
| 2004/0116887 A1 | 6/2004 | Thorson et al. | |
| 2004/0122405 A1 | 6/2004 | Van Gompel et al. | |
| 2004/0122406 A1 | 6/2004 | Moser et al. | |
| 2004/0127878 A1 | 7/2004 | Olson et al. | |
| 2004/0133180 A1 | 7/2004 | Mori et al. | |
| 2004/0192140 A1 | 9/2004 | Schneider et al. | |
| 2004/0197588 A1 | 10/2004 | Thomas et al. | |
| 2004/0241389 A1 | 12/2004 | Chung et al. | |
| 2004/0243086 A1 | 12/2004 | Van Gompel et al. | |
| 2005/0010186 A1 | 1/2005 | Otsubo et al. | |
| 2005/0101216 A1 | 5/2005 | Middlesworth et al. | |
| 2005/0106980 A1 | 5/2005 | Abed et al. | |
| 2005/0133151 A1 | 6/2005 | Maldonado Pacheco et al. | |
| 2006/0148358 A1 | 7/2006 | Hall et al. | |
| 2007/0233034 A1 | 10/2007 | Hildeberg et al. | |
| 2008/0000003 A1 | 1/2008 | Melander | |
| 2008/0033387 A1 | 2/2008 | Wastlund-Karlsson et al. | |
| 2009/0221982 A1 | 9/2009 | Cecconi et al. | |
| 2009/0306616 A1 | 12/2009 | Wennerback | |
| 2010/0036355 A1 | 2/2010 | Hakansson et al. | |

FOREIGN PATENT DOCUMENTS

| | | |
|---|---|---|
| EP | 0302957 A1 | 2/1989 |
| EP | 0 304 957 A2 | 3/1989 |
| EP | 0 360 929 A1 | 4/1990 |
| EP | 0 409 307 B1 | 1/1991 |
| EP | 0 418 493 A1 | 3/1991 |
| EP | 0 486 006 B1 | 9/1996 |
| EP | 0 861 647 A2 | 9/1998 |
| EP | 0 714 351 B1 | 12/1998 |
| EP | 0 605 012 B1 | 3/1999 |
| EP | 0 604 731 B1 | 6/1999 |
| EP | 1 184 022 A2 | 3/2002 |
| EP | 1 035 818 B1 | 4/2002 |
| EP | 1 384 459 A2 | 1/2004 |
| EP | 1 473 008 | 11/2004 |
| FR | 2 586 558 | 3/1987 |
| FR | 2 810 879 | 1/2002 |
| GB | 2-284 538 A | 6/1995 |
| JP | 06255006 A | 9/1994 |
| JP | 07-252762 | 10/1995 |
| JP | 9-286085 A | 11/1997 |
| JP | 10-043235 A | 2/1998 |
| JP | 11-276523 A | 10/1999 |
| JP | 2002 058 703 | 2/2002 |
| JP | 2002-65740 A | 3/2002 |
| JP | 2002-172137 A | 6/2002 |
| JP | 2002-520090 T | 7/2002 |
| JP | 2002-273808 A | 9/2002 |
| JP | 2003-520146 | 7/2003 |
| JP | 2003-290284 | 10/2003 |
| JP | 2004-050621 A | 2/2004 |
| JP | 2004-098356 A | 4/2004 |
| JP | 2004-519270 | 7/2004 |
| JP | 2005-511345 A | 4/2005 |
| JP | 2006-511274 A | 4/2006 |
| RU | 2 008 774 | 3/1994 |
| RU | 2 221 531 | 1/2004 |
| SU | 965339 | 10/1982 |
| TW | 233473 | 11/1994 |
| WO | WO 95/19258 | 7/1995 |
| WO | WO 96/10979 A1 | 4/1996 |
| WO | WO 97/29722 A1 | 8/1997 |
| WO | WO 97/34037 A1 | 9/1997 |
| WO | WO 98/37847 A1 | 9/1998 |
| WO | WO 99/27876 A1 | 6/1999 |
| WO | WO 99/32164 A1 | 7/1999 |
| WO | WO 00/02511 | 1/2000 |
| WO | WO 00/45764 A1 | 8/2000 |
| WO | WO 01/30563 A1 | 5/2001 |
| WO | 0145927 | 6/2001 |
| WO | WO 01/45927 A1 | 6/2001 |
| WO | WO 01/53076 | 7/2001 |
| WO | WO 2005/122984 A1 | 4/2002 |
| WO | WO 2005/122985 A1 | 4/2002 |
| WO | WO 02/34185 | 5/2002 |
| WO | WO 02/49560 A1 | 6/2002 |
| WO | WO 03/004748 A1 | 1/2003 |
| WO | WO 03/019714 A1 | 3/2003 |
| WO | 03047488 | 6/2003 |
| WO | WO 2004/058120 A1 | 7/2004 |
| WO | WO 2004/060251 A1 | 7/2004 |
| WO | WO 2004/078083 A1 | 9/2004 |
| WO | WO 2005/095700 A1 | 10/2005 |
| WO | WO 2006/038837 A1 | 4/2006 |

(56) References Cited

FOREIGN PATENT DOCUMENTS

| WO | WO 2006/093443 A1 | 4/2006 |
| WO | WO 2006/093439 A1 | 9/2006 |
| WO | WO 2006/093440 A1 | 9/2006 |
| WO | WO 2007/114744 A1 | 10/2007 |
| WO | WO 2008/060194 A1 | 5/2008 |

OTHER PUBLICATIONS

An English Translation of the Notice of Reasons for Rejection issued in the corresponding Japanese Patent Application No. 2007-517994 dated Nov. 24, 2009.

An English Translation of the Notice of Reasons for Rejection issued in the corresponding Japanese Patent Application No. 2007-557957 dated Feb. 9, 2010.

International Search Report from PCT/SE2005/000318.

Written Opinion from PCT/SE/2005/000318.

Hildeberg et. al, Copending U.S. Appl. No. 11/630,371, filed Dec. 21, 2006 entitled "Absorbent Article Comprising an Elastic Laminate Material".

Karlson et al., Copending U.S. Appl. No. 11/576,497, filed Dec. 3, 2008 entitled "Absorbent Article Comprising an Elastic Web Material".

Wastlund-Karlssson et al., Copending U.S. Appl. No. 11/630,372, filed Dec. 21, 2006 entitled "Absorbent Article Comprising an Elastic Laminate".

Wennerback, Copending U.S. Appl. No. 12/446,297, filed Apr. 20, 2009 entitled "Absorbent Article Comprising an Elastic Laminate".

Norrby et al., Copending U.S. Appl. No. 12/447,694, filed Apr. 29, 2009 entitled "Elastic Laminate and Absorbent Article Comprising the Laminate".

Wennerback, Copending U.S. Appl. No. 12/514,086, filed May 8, 2009 entitled "Absorbent Article Comprising an Elastic Laminate Material".

Non-Final Office Action in Copending U.S. Appl. No. 11/630,372 to Wastlund-Karlson et al. dated Sep. 16, 2009.

Final Office Action in Copending U.S. Appl. No. 11/630,372 to Wastlund-Karlson et al. dated Mar. 2, 2008.

Non-Final Office Action in Copending U.S. Appl. No. 11/630,372 to Wastlund-Karlson et al. dated Jul. 8, 2009.

Non-Final Office Action in Copending U.S. Appl. No. 11/630,371 to Hildeberg et al. dated Oct. 5, 2009.

Sueo Kawabata, "The Standardization and Analysis of Hand Evaluation", Second Edition, The Hand Evaluation and Standardization Committee, The Textile Machinery Society of Japan, published by the Textile Machinery Society of Japan, Osaka, Japan, Jul. 1980—Textile Machinery Japan.

International Preliminary Report on Patentability for PCT/SE2005/000318.

English language translation of an Official Action dated Dec. 14, 2010, issued by the Japanese Patent Office in corresponding Japanese Patent Application No. 2007-557957.

Official Inquiry issued Jan. 4, 2011, in Japanese Patent Application No. 2007-517993 (5 pages).

Notice of Reasons for Rejection issued Jun. 12, 2012, in Japanese Patent Application No. 2007-534537 (3 pages).

Official Inquiry issued Oct. 11, 2011, in Japanese Patent Application No. 2007-534537 (4 pages).

Notice of Reasons for Rejection issued Jan. 26, 2010, in Japanese Patent Application No. 2007-534537 (4 pages).

Office Action issued May 26, 2010, in Australian Patent Application No. 2004323904 (2 pages).

\* cited by examiner

UNDERWEAR ARTICLE COMPRISING AN ELASTIC LAMINATE

CROSS-REFERENCE TO RELATED APPLICATIONS

The present application is a continuation of PCT/SE2005/000318, filed on Mar. 2, 2005, and which designates the U.S. The entire contents of PCT/SE2005/000318 are incorporated herein by reference.

TECHNICAL FIELD

The present invention refers to a pant type underwear article, said article comprising front, back, crotch and waist regions. At least part of the article comprises an elastic laminate composed of two layers of fibrous material and an elastic film layer located between the fibrous layers.

BACKGROUND

It is known to hold disposable absorbent bodies in place against the body of an incontinent wearer with reusable pant-type underwear articles. The disposable absorbent bodies may be sanitary napkins or incontinence articles. This approach has advantages over conventional absorbent articles with an integral absorbent core such as diapers or incontinence pants, in that only the absorbent component of the article is disposed after soiling, while the underwear component can be reused, thus providing savings in both manufacturing costs and materials.

Laminate-type materials are known as components of absorbent articles such as diapers. For example, WO 03/047488 discloses an elastic laminate comprising an elastic film which on opposite sides is bonded to first and second non-elastic fibrous layers. The laminate is made by bonding the non-elastic fibrous layers to the elastic film layer and subsequently stretching the composite material, causing the non-elastic materials to break. The elastic film material may be of a breathable material. The laminate may be incorporated in an absorbent article, such as a diaper. No mention is made of the puncture resistance of such a material. The process described in WO 03/047488 will give a material which is soft and elastic, but which on the other hand has low resistance to puncturing, as the broken outer nonwoven layers will make no contribution to the puncture resistance of the laminate.

EP0861647 discloses an underwear system comprising a reusable underpant part and an exchangeable absorber lining. The pants consist of a 3-layer laminate, which contains a membrane film as an intermediate layer between two textile structures.

Elastic materials, such as stretch-bonded laminates, are also known. Such laminates may include a layer of melt-blown elastomeric fibers which have been stretched and sandwiched between outer layers of spunbonded webs.

US2003/0022582 describes a laminate in which an elastomeric film is bound between two or more layers of nonwoven webs. The laminate is said to be particularly useful in elastic "ears" of diapers, which allow the diaper to be stretched to accommodate variously sized wearers. It is stated that nonwoven materials provide little or no puncture resistance, hence any puncture resistance which the laminate has will be almost exclusively due to the puncture resistance of the elastomeric film.

However, there is room for improvement of the underwear articles used in two-component systems. The consumer places high demands on the comfort, fit and cloth-like feel of the pant-type underwear articles. Discreteness of the article is also a high priority, so the underwear article should be thin, preferably equally as thin as a pair of ordinary cotton pants. Furthermore, it is highly desirable that the absorbent body is held correctly in position against the wearer's body by the underwear article, so that it is optimally positioned to receive body exudates and undesired slippage or movement of the absorbent body is avoided. The underwear article itself is intended to be re-used, and therefore requires washing. It must therefore be able to tolerate the elevated temperatures, water, detergents and mechanical agitation which are present in the washing and/or drying machines of today without breaking. There is therefore a need for improvement of the strength of underwear articles, particularly their resistance to puncture.

OBJECT AND SUMMARY

One object of the present disclosure is to provide a pant-type underwear article which combines the properties of comfort and fit to the wearer's body and a soft and cloth-like feeling close to textile materials. It is further desirable that the article can be put on and taken off without puncturing, e.g. by fingernails. This is an important feature, as the force which can be applied during putting on and taking off such an article has been estimated as being up to 5N. It is also an object that the article should tolerate machine washing and drying and remain intact. These and further objects have been accomplished by a pant-type underwear article comprising front, back, crotch and waist regions, at least part of said article comprising an elastic laminate composed of first and second layers of fibrous material and an elastic film layer located between said first and second fibrous layers. The elastic laminate has a puncture resistance of at least 15N.

Due to the materials and methods involved in its construction, the puncture resistance of this laminate is higher than the elastic film layer alone (i.e. the layers of fibrous material contribute to the puncture resistance of the laminate). The underwear article provides good fit due to the elasticity of the laminate, and a cloth-like feel. Furthermore, the underwear article is reusable, and tolerates machine washing/drying, even machine washing up to 60° C. Use of the laminate allows the article to survive machine washing at least three times at up to 60° C. through a washing cycle of a washing machine and yet remain intact. The underwear article may be used to hold individual absorbent bodies (e.g. sanitary napkins or incontinence articles) securely in place against the user's body, yet will not be permanently fastened to such absorbent bodies. The elastic properties of the laminate help to ensure that the absorbent bodies are held securely against the wearer's body.

Preferably the elastic laminate has a puncture resistance of at least 20N, more preferably at least 30N.

In one embodiment, at least the front region of the article comprises the elastic laminate. Furthermore, both the front and back regions of the article may comprise the elastic laminate. In another embodiment, a substantial part of the crotch region of the article is free from elastic laminate. Additionally, the waist region of the article may be free from elastic laminate. In a separate embodiment, the entire article comprises the elastic laminate.

Preferably, the elastic film layer is breathable. The elastic laminate suitably has a Water Vapour Transmission Rate according to ASTM E96-00 Procedure D of at least 1500 g/m$^2$ 24 h, preferably at least 3000 g/m$^2$ 24 h.

In one embodiment, the elastic laminate has an elasticity in the transverse direction of the article of at least 30%, preferably at least 50%, more preferably 70%, when measured according to the elasticity test specified herein. Elasticity in the transverse direction of the article allows an article of a single size to be used on wearers having a variety of waist sizes. At least one of the layers of fibrous material may have an elongation at maximum load greater than the elasticity of the elastic laminate. Furthermore, both layers of fibrous material may have an elongation at maximum load greater than the elasticity of the elastic laminate.

According to one embodiment, the layers of fibrous material have an elongation at maximum load of at least 10%, preferably at least 20% greater than the elasticity of the elastic laminate. The first and/or the second layers of fibrous material preferably comprise a mixture of polypropylene and polyethylene polymers.

In a most preferred embodiment, the elastic laminate comprises first and second fibrous layers of spunbond material, each having a basis weight of between 10 and 35 g/m$^2$, preferably between 12 and 30 g/m$^2$, more preferably between 15 and 25 g/m$^2$ and a breathable elastic film layer having a basis weight between 20 and 100 g/m$^2$, preferably between 20 and 60 g/m$^2$, said elastic laminate having a Water Vapour Transmission Rate according to ASTM E96-00 Procedure D of at least 1500 g/m$^2$ 24 h, preferably at least 3000 g/m$^2$ 24 h.

DETAILED DESCRIPTION OF PREFERRED EMBODIMENTS

Figure 1:
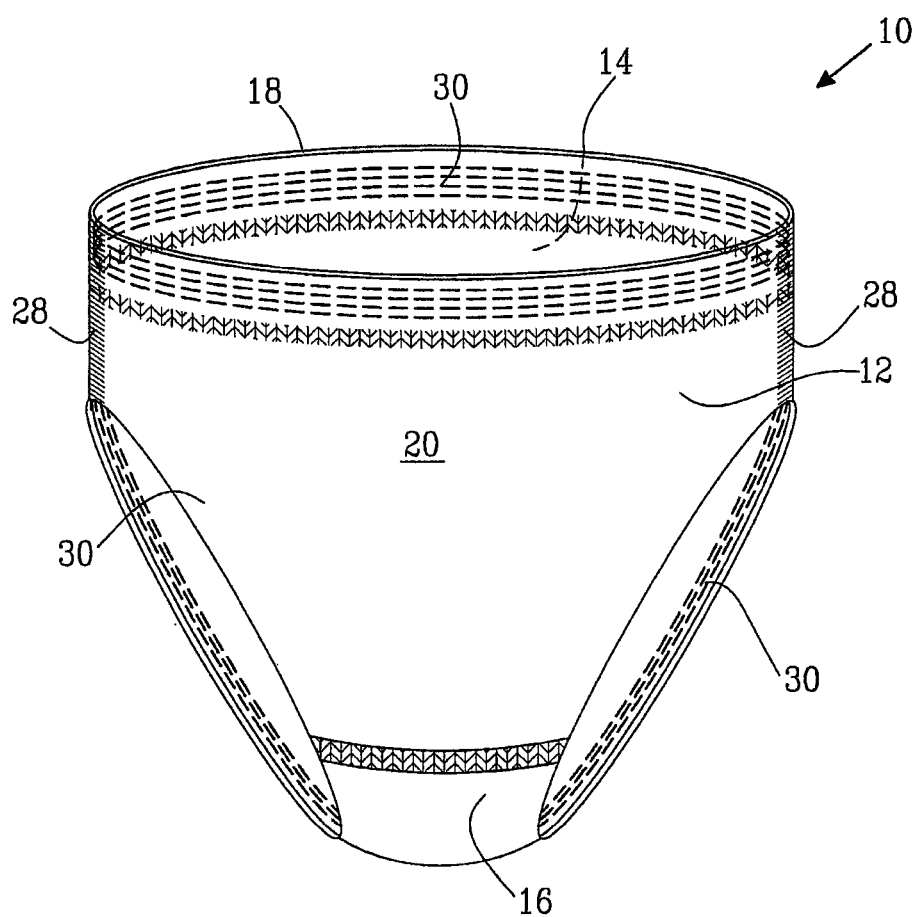
FIG. 1 shows a perspective view of a pant-type underwear article according to an embodiment of the present invention.

The figures show an embodiment of a pant-type underwear article 10. The article typically comprises front 12, back 14, crotch 16 and waist 18 regions. The front region 12 is that which in use covers the belly of the user. The waist region 18 is that which encircles the waist of the user when the article is being worn. The back region 14 is that which covers the lower torso/buttocks of the user when the article is being worn. The crotch region 16 is defined as the narrow part of the article intended to be worn in the wearer's crotch between the legs. The article 10 has a longitudinal (y) and a transverse direction (x).

Figure 2:
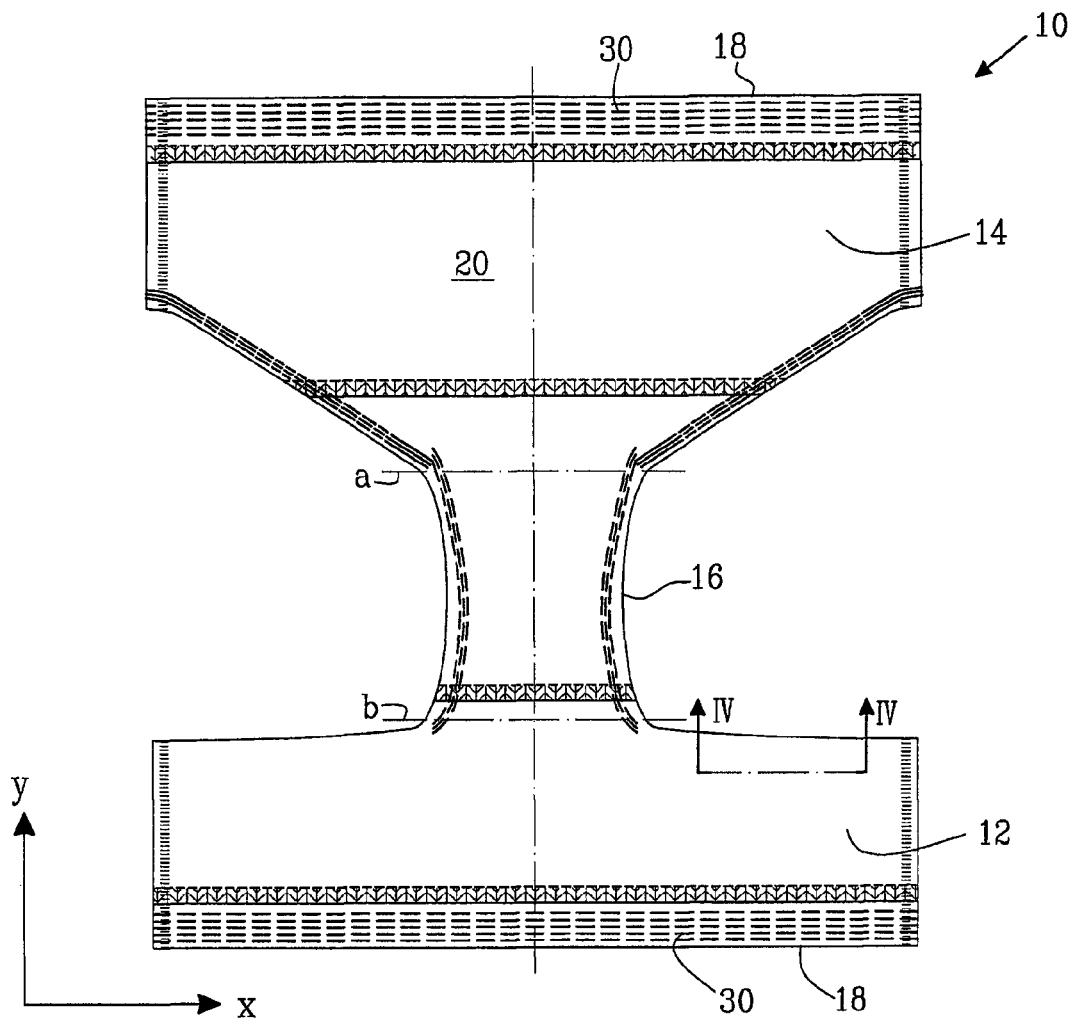
FIG. 2 shows is a simplified plan view of the pant-type underwear article in its flat, uncontracted state prior to formation.
Figure 3:
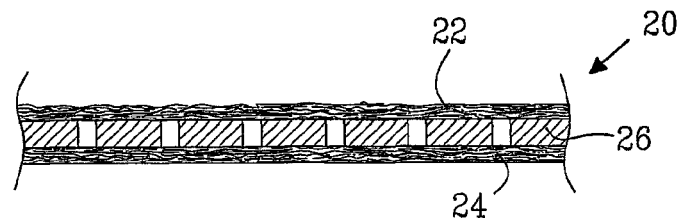
FIG. 3 is a cross section through an elastic laminate according to an embodiment of the invention.

The article is thus divided into four regions (front region 12, back region 14, crotch region 16 and waist region 18) in its longitudinal direction, as shown in FIG. 2. The front region is defined by the edge of the article at which the waist region ends, the longitudinal side edges of the article, part of the leg openings of the article and a transverse line (a) which is located at the point at which the angle of the edge of the leg opening changes most abruptly (i.e. the point at which the rate of change of the angle of the edge of the leg opening with respect to the transverse direction is highest). The back region is defined in a similar manner: by the edge of the article at which the waist region ends, the longitudinal side edges of the article, part of the leg openings of the article and a transverse line (b) which is located at the point on the edge of the leg opening at which the angle of the edge changes most abruptly (i.e. the point at which the rate of change of the angle of the edge of the leg opening with respect to the transverse direction is highest). The crotch region is defined at its longitudinal edges by the edges of the leg openings of the article and at its transverse edges by the two transverse lines (a) and (b) described above.

Elastic Laminate

At least part of the article 10 comprises an elastic laminate 20 composed of first 22 and second 24 layers of fibrous material and an elastic film layer 26 located between said first and second fibrous layers 22; 24. Characteristically, the elastic laminate 20 has a puncture resistance of at least 15N. Preferably, the elastic laminate 20 has a puncture resistance of at least 20N, more preferably at least 30N.

The laminate is elastic at least in the transverse x-direction of the article. The elasticity in the x-direction should be at least 30%, preferably at least 50%, more preferably at least 70%, as measured by the elasticity test specified herein.

The elastic laminate 20 is composed of first and second outer layers of fibrous material 22 and 24 and a middle elastic film layer 26 located between said fibrous layers. The outer fibrous layers 22 and 24 are chosen so that they, in combination with the inner elastic film layer, give the laminate high resistance to puncture. They also provide a soft and cloth-like feel to the laminate. Examples of suitable materials are carded webs and spunbond materials. The basis weight of the fibrous material layers should be between 10 and 35 g/m$^2$, preferably between 12 and 30 g/m$^2$, more preferably between 15 and 25 g/m$^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

The middle elastic film layer 26 is according to one embodiment of the invention an apertured elastic film having a basis weight between 20 and 100 g/m$^2$, preferably between 20 and 60 g/m$^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

As mentioned previously, the elastic film layer 26 may be breathable. This allows a higher degree of comfort for the wearer, as moisture/humidity build-up is reduced or completely avoided. The breathability of the elastic film layer 26 may be quantified by the Water Vapour Transmission Rate (WVTR) according to ASTM E96-00 Procedure D. According to one embodiment, the elastic laminate 20 has a Water Vapour Transmission Rate of at least 1500 g/m$^2$ 24 h, preferably at least 3000 g/m$^2$ 24 h as measured by the above ASTM procedure.

The elastic laminate 20 may be manufactured according to a modified version of the method disclosed in WO 03/047488, wherein one spunbond layer 22 is applied to the film 26 in a tacky state and will thus bond to the film layer, while the other spunbond layer 24 is adhesively laminated to the film layer 26, using for example a pressure sensitive hot melt adhesive. The modification involves the laminate being incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

In contrast to the method described in WO 03/047488, upon manufacture of a laminate according to an embodiment of the present invention, at least one, preferably both fibrous layers which are bound to the elastic film are not completely torn. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Therefore, at least one of—alternatively both—the layers of fibrous material 22, 24 may have an elongation at maximum load greater than the elasticity of the elastic laminate 20. Preferably the layers of fibrous material 22; 24, or at least one of the fibrous layers, have an elongation at maximum load that is at least 10%, preferably at least 20%, greater than the elasticity of the laminate 20.

According to a most-preferred embodiment of the invention, the elastic laminate 20 comprises first and second fibrous layers 22, 24 of spunbond material, each having a basis weight of between 10 and 35 g/m$^2$, preferably between 12 and 30 g/m$^2$, more preferably between 15 and 25 g/m$^2$ and a breathable elastic film layer 26 having a basis weight between 20 and 100 g/m$^2$, preferably between 20 and 60 g/m$^2$. The elastic laminate 20 according to this embodiment has a Water Vapour Transmission Rate according to ASTM E96-00 Procedure D of at least 1500 g/m$^2$24 h, preferably at least 3000 g/m$^2$24 h.

Figure 4:
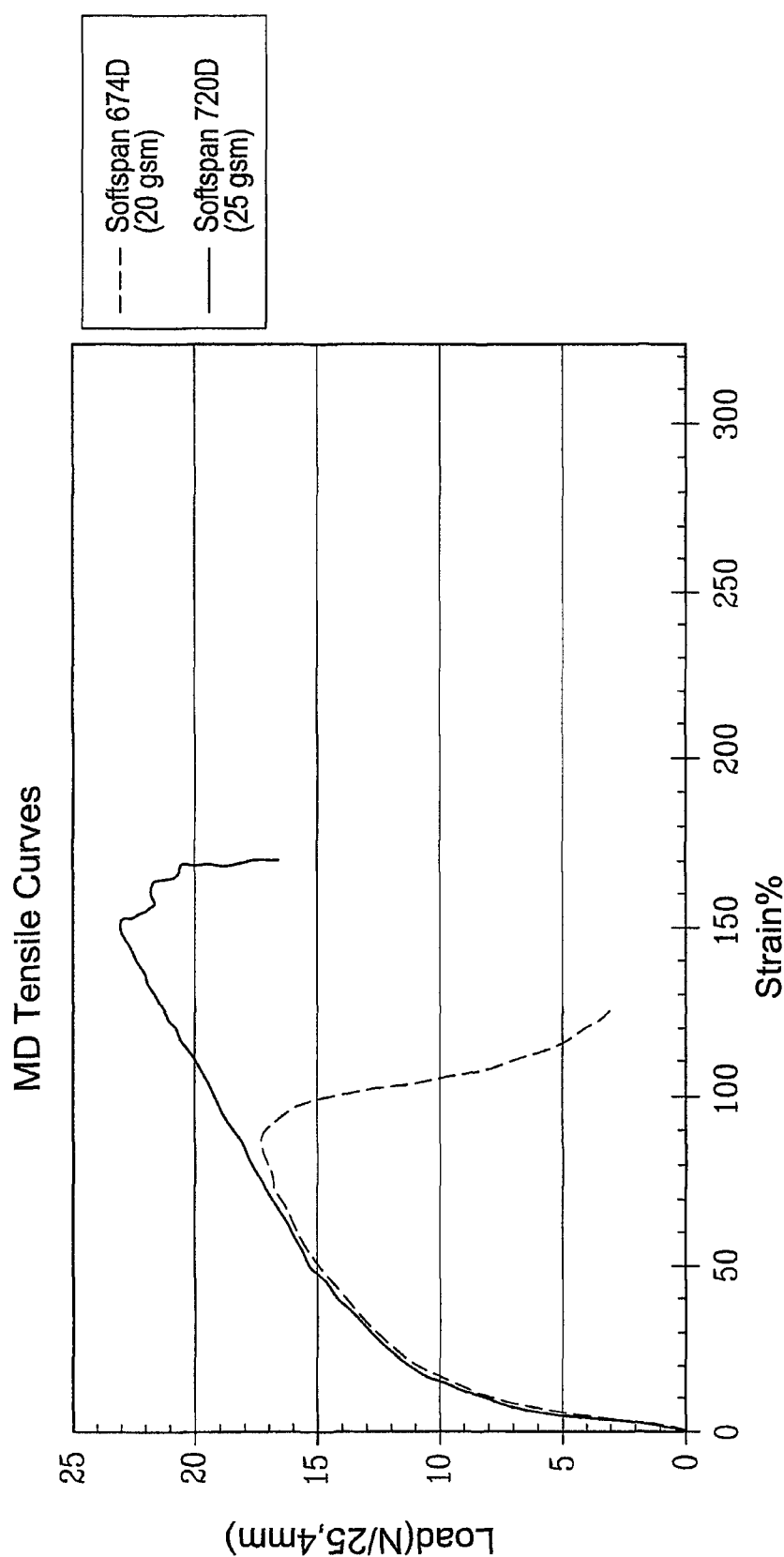
FIG. 4 is a graph showing load vs. strain for two nonwoven fibrous layers.

FIG. 4 shows the behaviour of two 20 gsm and 25 gsm nonwoven layers (BBA Sofspan 200) under stretching. It can be seen that, with increasing load (in Newtons), the strain in the layer increases, first slowly and then more rapidly. The applied load eventually reaches a maximum (the "maximum load"), at which point the load drops rapidly as the material fails. It can be seen that for the 20 gsm layer, maximum load is reached at around 90% strain, while for the 25 gsm layer, maximum load is reached at around 150% strain.

Figure 5:
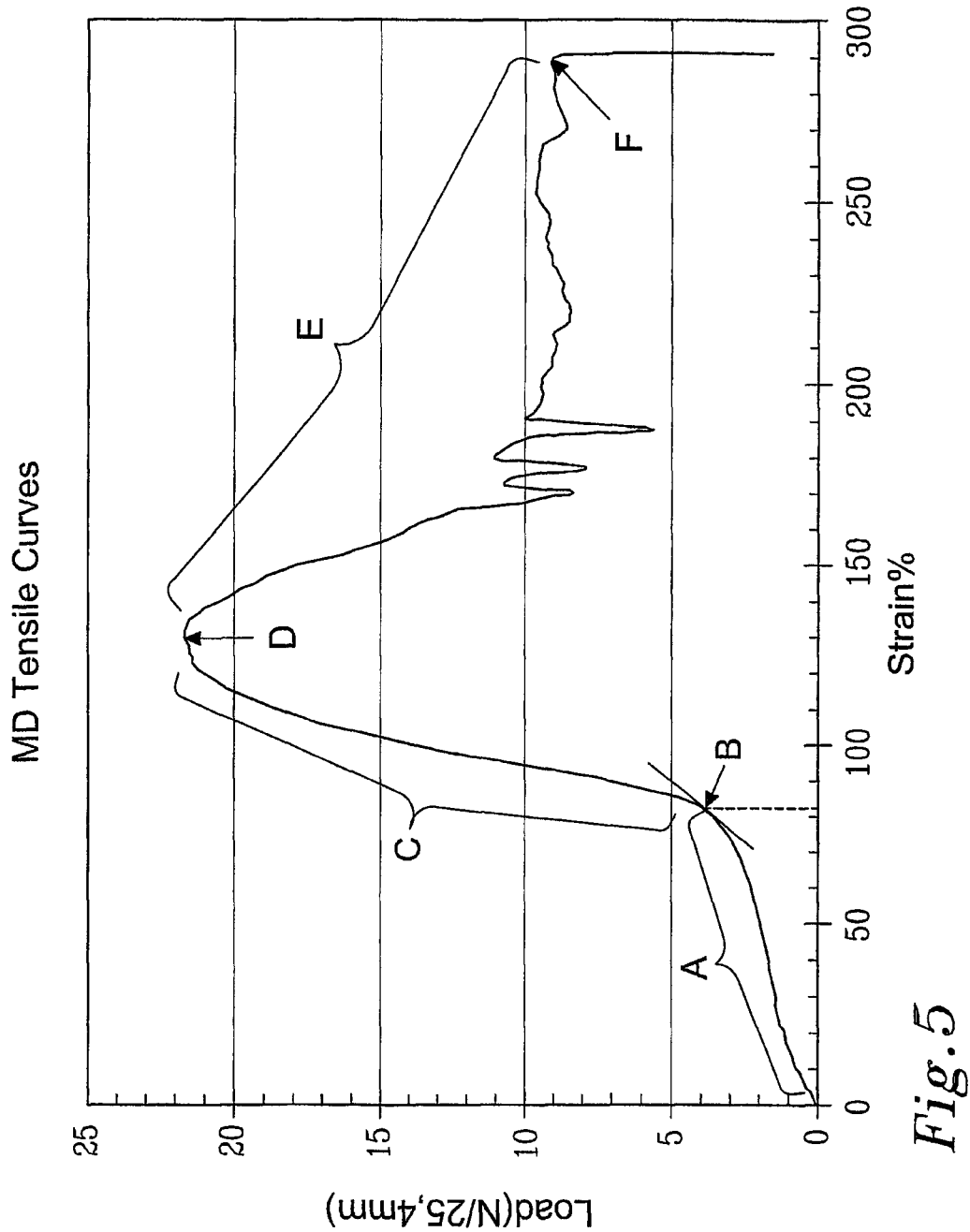
FIG. 5 is a graph showing load vs. strain for an elastic laminate.
Figure 6:
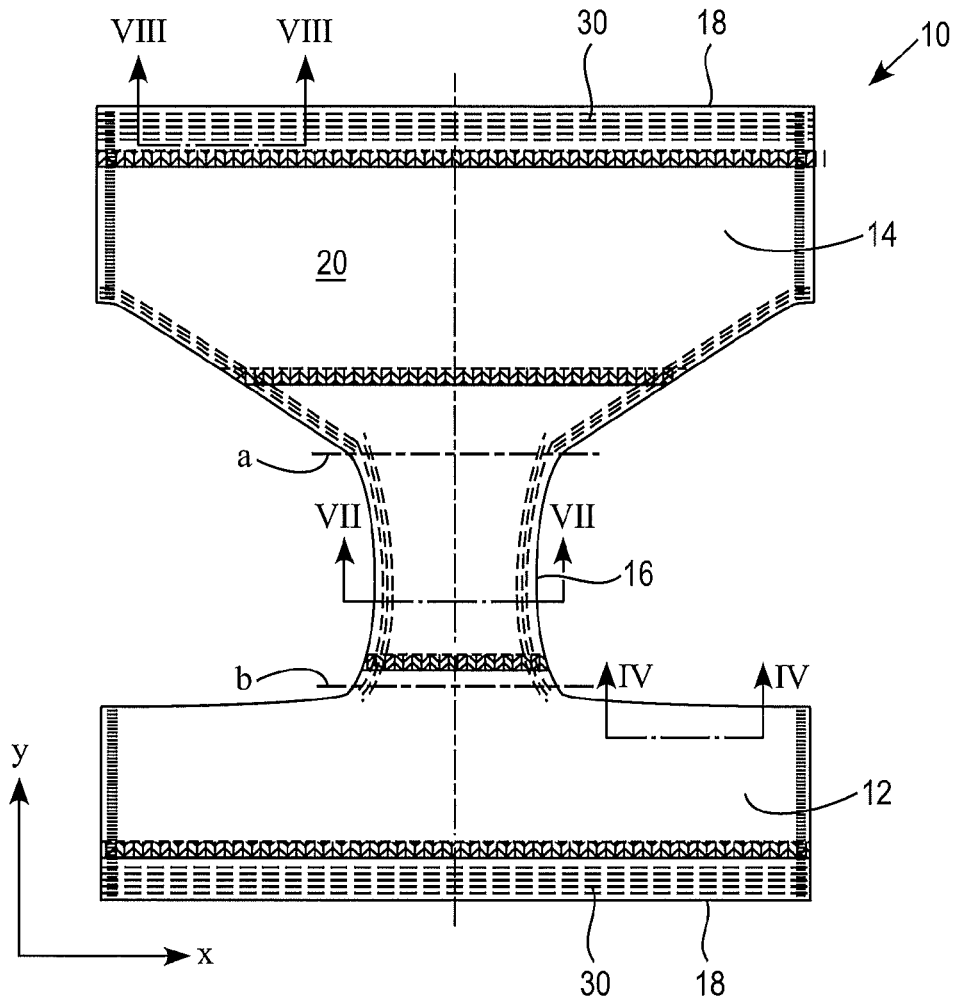
FIG. 6 shows a pant-type underwear article made of waist regions 18, a front region 12, a back region 14 and a crotch region 16. The waist and the crotch regions are free of an elastic laminate.
Figure 7:
FIG. 7 shows the cross section VII-VII in FIG. 6. This is a cross-section of the crotch region comprising a nonwoven material (40) and elastic threads (41) near the longitudinal edges.
Figure 8:
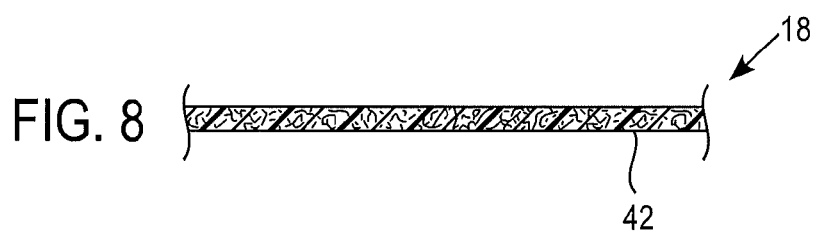
FIG. 8 shows the cross-section VIII-VIII in FIG. 6. This is a cross-section of the waist region comprising a nonwoven material (42).

FIG. 5 shows the behaviour of a laminate according to the present invention under stretching at a constant strain. The laminate comprises 25 gsm Sofspan NW from BBA on both sides of a 40 gsm apertured elastic film, where one face is glue-laminated with approximately 5 gsm glue.

From zero strain, the laminate exhibits elastic behaviour in region (A) up to around a "knee point" (B), after which, the load increases rapidly through region (C). The knee point (B) is defined as the first point on the load-strain curve at which the gradient becomes greater than 0.3N/%. The laminate shown is elastic up to about 80% strain—as this is less than the elongation (strain) at maximum load of the nonwoven layer (ca. 150% from FIG. 5), the laminate falls within the present invention.

The applied load eventually reaches a maximum (the "maximum load", D), at which point the gradient of the load-strain curve is zero. The load then drops through region (E) as the material fails. Complete failure of the laminate occurs at point (F).

It is preferred that the elastic laminate 20 has a breathability (Water Vapour Transmission Rate) according to ASTM E96-00 Procedure D of at least 1500 g/m$^2$ 24 h, preferably at least 3000 g/m$^2$ 24 h.

The opacity of a material layer is the characteristic ability of the material layer to visually hide from view an underlying object or pattern. The opacity is measured in %, wherein 100% opacity means that nothing can be seen through the material layer and 0% means that the material layer is completely transparent. The opacity is measured by the Opacity Test described below, which is based on luminous-reflectance-factor data. The elastic web material has an opacity of at least 40%, preferably at least 50% and more preferably at least 60%. The opacity of the elastic web material provides a cloth-like appearance to the article, which is of particular importance when the article is pant-type underwear. Especially in this case, where the elastic web material forms the sole component in large areas of the front and back regions, the appearance of the elastic web material is of great importance for the overall appearance of the article. Thus by making the elastic web material opaque with an opacity of at least 40%, the pant-type underwear article will appear more cloth-like and more like "normal" underwear, than if the elastic web material has a higher degree of transparency.

Opacity can be increased by the incorporation of opacifying fillers into the laminate, particularly into the elastic film. Such pigments can be organic or inorganic dyes, colouring agents, or whitening agents. Inorganic materials such as titanium dioxide, inorganic carbonates, synthetic carbonates, talc, nepheline syenite, magnesium hydroxide, aluminium trihydrate siatomaceous earth, mica, natural or synthetic silicas, calcinated clays and mixtures thereof are preferred examples of opacifying fillers.

The filler is preferably added as a master batch at the extrusion of the film. One example of an appropriate concentration is about 5% filler by weight of the film.

The open area of the elastic film layer is preferably at least 5%, more preferably at least 8%. The open area is measured by image analysis methods and is defined as the sum of the hole area divided by the total area of the film sample.

Pant-type Underwear Article

The pant-type underwear article 10 disclosed in FIG. 1 is intended to enclose the lower part of the wearer's trunk and crotch region. It comprises front 12, back 14, crotch 16 and waist regions 18. The front 12 and back 14 regions are joined to each other along their longitudinal edges at side seams 28, which may comprise ultrasonic welds, glue strings or the like.

The entire article 10 may comprise elastic laminate 20. Preferably, at least the front region 12 of the article 10 comprises the elastic laminate 20. Furthermore, both the front and back regions 12; 14 of the article may comprise the elastic laminate 20.

According to a preferred embodiment a substantial part of the crotch region 16 of the article is free from the elastic laminate 20. A "substantial part" used herein refers to at least 50%, preferably at least 75%. If the crotch region 16 does not comprise elastic laminate 20, it may comprise nonwoven material, or a breathable film material. This embodiment allows improved comfort and breathability of the article in the crotch region. Alternatively, the crotch region 16 may comprise a different nonwoven film laminate than the elastic laminate 20 used in the remainder of the article. As a further alternative, the crotch region 16 may comprise a plastic film material, which may be non-breathable.

Preferably also the waist region 18 of the article is free from the elastic laminate. The waist region 18 may comprise a nonwoven material that is elasticized by elastic members 30, such as elastic threads, contractably affixed between material layers, such as nonwoven materials. Such elastic members 30 may also be arranged around the leg openings of the article. Ultrasonic welds, glue strings or the like, join the elastic laminate 20 to the elasticized nonwoven in the waist region 18.

No additional elasticized side panels joining the front and back regions 12 and 14 are needed when using the elastic laminate 20 according to the invention. If desired, additional elasticized side panels may of course be provided, especially in cases where the elastic laminate 20 is arranged only in parts of the front and/or back regions.

The elastic laminate should have a puncture resistance of at least 15N as measured according to ASTM Designation D3763-02. Preferably, the elastic laminate of the present invention has a puncture resistance of at least 20N, and more preferably at least 30N.

The elastic laminate should preferably have a softness according to Kawabata of at least 20, preferably at least 30 and most preferably at least 40.

It is further desired that it has a formability according to Kawabata of no more than 50, preferably no more than 30, more preferably no more than 20 and most preferably no more than 10.

It is also desired that the elastic laminate has a drapability according to Kawabata of no more than 40.

Description of Test Methods

Opacity

The opacity of the elastic web material is measured according to a slightly modified version of SS-ISO 2471: 1998 by the Swedish Standard Institute (Diffuse Reflectance Method). The method is originally intended for measuring the opacity for paper sheets, but it also functions well for measuring the opacity of other types of sheet materials, such as elastic laminates according to this invention. The opacity is measured in an unstretched condition of the elastic web material. The principle of the test method is to measure the Single-Sheet Luminous Reflectance Factor, $R_0$, through a single sheet against a standardized black backing and the Intrinsic Luminous Reflectance Factor, $R_\infty$, against a completely opaque white backing. The opacity (%) is calculated from the formula $100 \cdot R_0/R_\infty$.

The following modifications of the test method were made:

i) When measuring the Single-Sheet Luminous Reflectance Factor, $R_0$, a black velvet fabric was used as backing.

ii) When measuring the Intrinsic Luminous Reflectance Factor, $R_\infty$, the measurement was made on one single sheet of the elastic laminate against a white tile as backing.

iii) The CIE illuminant D65 (10°) was used instead of the CIE illuminant C (2°).

The measured opacity values are mean values from five measurements.

Puncture Strength

Puncture strength is measured according to ASTM Designation D3763-02. From penetration impact-type tests, this method produces data of load versus displacement. The maximum load is calculated for each laminate.

Tensile Strength (Reference: ASTM D 882)

The method measures tensile strength and elongation of difference elastic materials. The tensile strength and elongation of a well-defined test piece is tested by means of a tensile tester.

Apparatus: Instron 4301

Tensile tester connected to a computer

Crosshead speed: 500 mm/min

Clamp distance: 50 mm

Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4 h in 50% RH±5% RH and 23° C.±2° C. before testing.

Procedure: The tensile tester is calibrated according to the apparatus instructions and set to zero. The sample is mounted and it is ensured that it is not obliquely or unevenly fastened. The material is prevented from slipping by using clamps covered with galloon or similar material. The tensile tester is started, and stopped after the material has broken (if not automatically controlled). Measurements resulting from premature failures (i.e. the sample breaks at the clamp, or is damaged during preparation) are ignored if possible.

The following results are expressed by the tensile tester/computer:

Maximum force, N/25.4 mm

Elongation at maximum force, %

Break force, N/25.4 mm

Elongation at break force, %

Knee point, N/%

Elasticity test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| Crosshead speed: | 500 mm/min |
|---|---|
| Clamp distance: | 50 mm |
| Preload: | 0.05 N |

The sample is placed in the clamps according to the marks and it is made sure that the sample is centred and fastened perpendicularly in the clamps. The tensile tester is started and three cycles between 0 and the predetermined elongation, equal to the highest defined 1 st load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

Kawabata Tests

The Kawabata KES-FB test is a Japanese quality judgment system for used for textile materials and is disclosed in "The Standardization and Analysis of Hand Evaluation (2nd Edition), Sueo Kawabata, July 1980, The Hand Evaluation and Standardization Committee, The Textile Machinery Society of Japan". The test used in this invention uses two of the Kawabata testing machines, KES-FB2 for measuring Bending rigidity, B ($gf \cdot cm^2/cm$), and KES-FB1 for measuring Shear stiffness, G ($gf/cm \cdot degree$) and Tensile strain, EMT (%).

Bending Rigidity (B) KES-FB2

The slope was measured between 0.5 cm−1 and 1.5 cm−1 and −0.5 cm−1 and −1.5 cm−1.

The measurements were performed in both directions (MD and CD) with the following settings:
Total sample area: 20×20 cm;
Maximum: curvature: Kmax=±2.5 cm−1;
Bending rate: 0.5 cm−$^1$/sec;
Sample effective dimension: 20 cm length and 1 cm width;
Bending deformation is applied to the width direction.

Shear stiffness (G) KES-FB1

The slope was measured between 0.5 cm$^{-1}$ and 2.5 cm$^{-1}$ and 0.5 cm$^{-1}$ and −2.5 $^{cm-1}$.

The measurements were performed in both directions (MD and CD) with the following settings:
Total sample area: 20×20 cm;
Tension of specimen: W=W=10 gf/cm;
Maximum shear angle: φ=±8°.
Sample effective dimension: 20 cm width and 5 cm length;
Shear deformation is applied to the width direction.

Tensile strain (EMT)

The measurements were performed in both directions (MD and CD) with the following settings:
Total sample area: 20×20 cm;
Maximum load: Fm=500 gf/cm;
Tensile speed: 0.2 mm/sec.
Sample effective dimension: 20 cm width and 2.5 cm length;
Tensile deformation is applied to the length direction.
Elongation sens 50 mm/10V.

Softness (S)

The Softness (S) according to Kawabata is obtained from the formula:

$$S = \sqrt{EMT/B}$$

Formability (F)

The Formability (F) according to Kawabata is obtained from the formula:

$$F = B \cdot EMT.$$

Drapability (D)

The Drapability (D) according to Kawabata is obtained from the formula:

$$D = 116 + 25 \cdot \log(B \cdot G/W), \text{ wherein W is the basis weight of the sample.}$$

EXAMPLES

Opacity

The opacity of an elastic laminate sample was measured. The sample was an elastic laminate according to the invention comprising an inner apertured three-layer elastic film of PE-SEBS-PE, basis weight 36 g/m$^2$ and two outer layers of spunbond material, PP (polypropylene), each having a basis weight of 22 g/m$^2$. The laminate is produced by a modified version of the method disclosed in WO 03/04788 and which is described above, wherein one spunbond layer is applied to the film in a tacky state and will thus bond to the film layer, while the other spunbond layer is adhesively laminated to the film layer using for example a pressure sensitive hot melt adhesive (glue amount 3 g/m$^2$). The laminate is incrementally stretched, at which the non-elastic spunbond layers are stretched to a point below the elongation at maximum load to retain some strength in the spunbond layers. The elasticity of the laminate after stretching is close to the elasticity of the elastic film layer.

The above-mentioned basis weights of the layers refer to the finished laminate after stretching. Before stretching the basis weight of the individual layers were: inner film layer 40 g/m$^2$, outer spunbond layers 25 g/m$^2$ each and glue layer 3 g/m$^2$. Since it is difficult to measure the basis weights of the individual layers after lamination and stretching an approximation has been made from the basis weights of the layers before lamination and stretching. The laminate before stretching had a total basis weight before stretching of 93 g/m$^2$ and after stretching it had a basis weight of 85 g/m$^2$, which means a deformation of about 10%. It is then assumed that the deformation of the individual fibrous layers and the film layer is the same, i.e. about 10%.

The inner film layer contained 4.9% by weight filler in the form of TiO2. The open area of the film layer was 13%. The opacity of the laminate was about 68%.

An opacity value of at least 40% is acceptable in order to provide the desired cloth-like appearance of the pant diaper disclosed above, which in considerable areas of the chassis contains the elastic laminate as the sole component. Preferably the opacity should be at least 50%, more preferably at least 60%.

It is further desired, for example for cost reasons, to have a low basis weight of the elastic laminate. The basis weight should be 100 g/m$^2$ or lower. The ratio Opacity/Basis Weight is therefore also an aspect of this invention. Preferably this ratio should be at least 0.4, more preferably at least 0.5 and most preferably at least 0.6, wherein opacity is measured in % and the basis weight is measured in g/m$^2$.

Puncture Resistance

The puncture resistance of three different samples (A, B and C) were measured according to ASTM Designation D3763-0$^2$ and are shown in Table 1.

Tensile Strength

The tensile strenth of three different samples (A, B and C) were measured according to the method given above and are shown in Table 1.

Elasticity

The elasticity of three different samples (A, B and C) were measured according to the method given above and are shown in Table 1. Sample A is an elastic laminate according to WO03/047488 with 15 gsm PP spunbond nonwoven on both sides of a 40 gsm elastic film. The used spunbond nonwoven has an elongation at maximum load of 60%, which is less than the elasticity of the laminate. The low puncture resistance of this material means that it falls outside the scope of the present invention.

Sample B is an elastic laminate with 25 gsm PP/PE spunbond nonwoven on both sides of a 36 gsm elastic film.

Sample C is an elastic laminate with one layer of 25 gsm PP/PE nonwoven and one layer of 20gsm PP/PE nonwoven on opposite sides of a 36 gsm elastic film.

TABLE 1

|  | Sample A | Sample B | Sample C |
|---|---|---|---|
| Puncture force (N) | 12.8 | 49.5 | 40.6 |
| Basis weight (gsm) | 78.66 | 87.96 | 82.71 |
| Tensile strength and Elongation MD (machine direction) | | | |
| Tensile strength at Peak (MD), N/25 mm | 8.29 | 25.3 | 28.03 |
| Elongation at break, % | 269.82 | 311.94 | 691.47 |
| Elongation at Peak/Deformation, % | 136 | 111.44 | 109.28 |
| CD (cross direction) | | | |
| Tensile strength at Peak (CD), N/25 mm | 11.72 | 11.15 | 9.16 |
| Elongation at break, % | 792.87 | 768.19 | 160.15 |
| Elongation at Peak/Deformation, % | 74.88 | 124.82 | 134.42 |
| Determination of load & unload forces and permanent elongation | | | |
| Tensile strength at 80% elongation (1st cycle) | 2.78 | 7.11 | 10.66 |
| Permanent Elongation (3rd cycle) | 7.86 | 7.52 | 8.09 |
| 3rd Retraction Forces | | | |
| At 80%, N/25 mm | 1.14 | 1.44 | 1.42 |
| At 60%, N/25 mm | 0.82 | 0.85 | 0.8 |
| At 40%, N/25 mm | 0.54 | 0.53 | 0.48 |

Kawabata Tests

Four different samples were measured in a Kawabata test with respect to Bending rigidity (B), Shear stiffness (G) and Tensile strain (EMT). From these measured values the Softness (S), Formability (F) and Drapability (D) were calculated.

The Four Samples Were:

Sample laminate (SL): an elastomeric laminate according to an embodiment of the invention comprising an inner apertured three-layer elastomeric film of PE-SEBS-PE, basis weight 36 g/m$^2$ and two outer layers of spunbond material, PP (polypropylene), each having a basis weight of 22 g/m$^2$. The laminate is produced by a modified version of the method disclosed in WO 03/04788 and which is described above, wherein one spunbond layer is applied to the film in a tacky state and will thus bond to the film layer, while the other spunbond layer is adhesively laminated to the film layer using for example a pressure sensitive hot melt adhesive (glue amount 3 g/m$^2$). The laminate is incrementally stretched, at which the non-elastic spunbond layers are stretched to a point below the elongation at maximum load to retain some strength in the spunbond layers. The elasticity of the laminate after stretching is close to the elasticity of the elastomeric film layer.

The above-mentioned basis weights of the layers refer to the finished laminate after stretching. Before stretching the basis weight of the individual layers were: inner film layer 40 g/m$^2$, outer spunbond layers 25 g/m$^2$ each and glue layer 3 g/m$^2$. Since it is difficult to measure the basis weights of the individual layers after lamination and stretching an approximation has been made from the basis weights of the layers before lamination and stretching. The laminate before stretching had a total basis weight before stretching of 93 g/m$^2$ and after stretching it had a basis weight of 85 g/m$^2$, which means a deformation of about 10%. It is then assumed that the deformation of the individual fibrous layers and the film layer is the same, i.e. about 10%.

Ref. 1: Cotton-knitted goods, so called jersey with elastomeric threads.

Ref. 2: Outer coversheet of Tena Discreet incontinence pant (odour control, size medium) produced by SCA Hygiene Products AB. The outer coversheet comprises two layers of nonwoven with parallel elastic threads there between, which wrinkle the material.

Ref. 3: Outer coversheet material of Poïse normal super incontinence pant produced by Kimberly-Clark. The outer coversheet comprises two layers of nonwoven with parallel elastic threads there between which wrinkle the material.

A climate conditioning of the materials were performed at 20° C. and 65% RH for 48 hours. For the pant products, the absorbent core was removed and the outer coversheet was stretched over a knitwear measuring device for 24 hours and was then allowed to relax in the same climate during 24 hours.

The sizes of the samples were 10×10 cm.

All tests were made on three samples and in two material directions (machine direction, MD, and cross direction, CD).

The following results were obtained.

TABLE 2

| Sample | B, Bending rigidity (gf · cm$^2$/cm) | | | G, Shear stiffness (gf/cm · degree) | | | EMT, Tensile strain (%) | | |
|---|---|---|---|---|---|---|---|---|---|
| | MD | CD | Mean | MD | CD | Mean | MD | CD | Mean |
| SL | 0.095 | 0.022 | 0.059 | 1.46 | 1.38 | 1.42 | 208.4 | 92.0 | 150.2 |
| Ref. 1 | 0.03 | 0.03 | 0.03 | 0.58 | 0.64 | 0.61 | 160.6 | 173.2 | 166.9 |
| Ref. 2 | 1.05 | 0.09 | 0.57 | 0.87 | 0.68 | 0.77 | 23.9 | 211.7 | 117.8 |
| Ref. 3 | 1.53 | 0.04 | 0.78 | 1.74 | 1.21 | 1.47 | 26.28 | 195.3 | 110.8 |

From these results the Softness (S), the Drapability (D) and the Formability (F) according to Kawabata were calculated according to the formulas stated above. These results are stated in Table 3 below.

TABLE 3

| Sample | Softness (S) $\sqrt{EMT/B}$ | Drapability (D) $116 + 25$ $\log(B \cdot G/W)$ | Formability (F) $B \cdot EMT$ | Basis Weight (W) g/m$^2$ |
|---|---|---|---|---|
| SL | 50 | 40 | 9 | 88 |
| Ref. 1 | 75 | 13 | 5 | 231 |
| Ref. 2 | 14 | 45 | 67 | 160 |
| Ref. 3 | 12 | 51 | 87 | 133 |

The results should be interpreted in the following way:

| | |
|---|---|
| Softness (S): | a higher value indicates a softer material. |
| Drapability (D): | a higher value indicates a stiffer material. |
| Formability (F): | a higher value indicates that the material is less formable. |

The test laminate according to an embodiment of the invention has a Softness (S) and a Formability (F) according to Kawabata which is close to cotton-knitted goods (Ref. 1). Also the Drapability (D) according to Kawabata is closer to the cotton-knitted reference material than the other two tested materials. Thus the use of the elastomeric laminate provides a pant article having a cloth-like feeling close to a cotton material. The pant will also have an excellent comfort and fit to the wearer's body. By using the elastomeric laminate only in those parts of the pant in which the properties of the material is best utilized, a very economic utilization of the material is accomplished.

It is preferred that the laminate has a Softness (S) according to Kawabata of at least 20, more preferably at least 30 and most preferably at least 40. It is also preferred that the laminate has a Formability (F) according to Kawabata of no more than 50, preferably no more than 30, more preferably no more than 20 and most preferably no more than 10. It is also preferred that the laminate has a Drapability (D) according to Kawabata of no more than 40.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. A pant underwear article, comprising front, back, crotch and waist regions, said article having a longitudinal direction and a transverse direction, at least part of the article comprising an elastic laminate composed of first and second layers of fibrous material and an elastic film layer located between said first and second fibrous layers, wherein said elastic laminate has a puncture resistance of at least 15N,
wherein at least one of the layers of fibrous material has an elongation at maximum load greater than an elasticity of the elastic laminate,
wherein a substantial part of the crotch region of the article is free from said elastic laminate,
wherein the entire waist region of the article is free from said elastic laminate,
wherein the pant underwear article does not contain an integral absorbent core,
wherein said first layer of fibrous material is in direct contact with a first side of said elastic film layer, and
wherein said second layer of fibrous material is adhesively laminated to a second side of said elastic film layer.

2. The article as claimed in claim 1, wherein the elastic laminate has a puncture resistance of at least 20N.

3. The article as claimed in claim 2, wherein at least the front region of the article comprises the elastic laminate.

4. The article as claimed in claim 1, wherein at least the front region of the article comprises the elastic laminate.

5. The article as claimed in claim 1, wherein both the front and back regions of the article comprise the elastic laminate.

6. The article as claimed in claim 1, wherein said elastic film layer is breathable.

7. The article as claimed in claim 6, wherein said elastic laminate has a Water Vapour Transmission Rate according to ASTM E96-00 Procedure D of at least 1500 g/m$^2$24 h.

8. The article as claimed in claim 7, wherein said elastic laminate has a Water Vapour Transmission Rate according to ASTM E96-00 Procedure D of at least 3000 g/m$^2$24 h.

9. The article as claimed in claim 1, wherein said elastic laminate has an elasticity in the transverse direction of the article of at least 30% when measured with an elasticity test method utilizing three tensile cycles, comprising stretching a sample of said article to be measured between 0 and an elongation 30%, thereafter relaxing the sample and measuring the permanent elongation (an elongation compared to the length of the sample before said three cycles), the permanent elongation being less than 10% of the length of the sample before the three cycles.

10. The article as claimed in claim 1, wherein both the layers of fibrous material have an elongation at maximum load greater than the elasticity of the elastic laminate.

11. The article as claimed in claim 1, wherein at least one of the layers of fibrous material have an elongation at maximum load of at least 10% greater than the elasticity of the elastic laminate.

12. The article as claimed in claim 1, wherein the first or second layer of fibrous material comprises a mixture of polypropylene and polyethylene polymers.

13. The article as claimed in claim 1, wherein said elastic laminate comprises first and second fibrous layers of spunbond material, each having a basis weight of between 10 and 35 g/m$^2$ and a breathable elastic film layer having a basis weight between 20 and 100 g/m$^2$, said elastic laminate having a Water Vapour Transmission Rate according to ASTM E96-00 Procedure D of at least 1500 g/m$^2$24 h.

14. The article as claimed in claim 1, wherein the elastic laminate has a puncture resistance of at least 30N.

15. The article as claimed in claim 1, wherein said elastic laminate has an elasticity in the transverse direction of the article of at least 50% when measured with an elasticity test method utilizing three tensile cycles, comprising stretching a sample of said article to be measured between 0 and an elongation 50%, thereafter relaxing the sample and measuring the permanent elongation (an elongation compared to the length of the sample before said three cycles), the permanent elongation being less than 10% of the length of the sample before the three cycles.

16. The article as claimed in claim 1, wherein said elastic laminate has an elasticity in the transverse direction of the article of at least 70% when measured with an elasticity test method utilizing three tensile cycles, comprising stretching a sample of said article to be measured between 0 and an elongation 70%, thereafter relaxing the sample and measuring the permanent elongation (an elongation compared to the length of the sample before said three cycles), the permanent elongation being less than 10% of the length of the sample before the three cycles.

17. The article as claimed in claim 1, wherein the layers of fibrous material have an elongation at maximum load of at least 10% greater than the elasticity of the elastic laminate.

18. The article as claimed in claim 1, the first and the second layers of fibrous material comprise a mixture of polypropylene and polyethylene polymers.

19. The article as claimed in claim 1, wherein said elastic laminate comprises first and second fibrous layers of spunbond material, each having a basis weight of between 15 and 20 g/m² and a breathable elastic film layer having a basis weight between 20 and 60 g/m², said elastic laminate having a Water Vapour Transmission Rate according to ASTM E96-00 Procedure D of at least 3000 g/m²24 h.

20. The article as claimed in claim 1, wherein the waist region of the article encircles a waist of a user when the article is being worn.

21. The article as claimed in claim 1, wherein the front and back regions do not extend into the waist region.

22. A pant underwear article, comprising front, back, crotch and waist regions, said article having a longitudinal direction and a transverse direction, at least part of the article comprising an elastic laminate composed of first and second layers of fibrous material and an elastic film layer located between said first and second fibrous layers, wherein said elastic laminate has a puncture resistance of at least 15N, wherein at least one of the layers of fibrous material has an elongation at maximum load greater than an elasticity of the elastic laminate, wherein a substantial part of the crotch region of the article is free from said elastic laminate, wherein the entire waist region of the article is free from said elastic laminate, wherein the pant underwear article is reusable after washing, wherein said first layer of fibrous material is in direct contact with a first side of said elastic film layer, and wherein said second layer of fibrous material is adhesively laminated to a second side of said elastic film layer.

23. The article as claimed in claim 22, wherein the waist region of the article encircles a waist of a user when the article is being worn.

24. The article as claimed in claim 22, wherein the front and back regions do not extend into the waist region.

* * * * *